(12) United States Patent
Greenhalgh

(10) Patent No.: US 6,494,909 B2
(45) Date of Patent: Dec. 17, 2002

(54) ENDOVASCULAR VALVE

(75) Inventor: E. Skott Greenhalgh, Wyndmoor, PA (US)

(73) Assignee: Prodesco, Inc., Perkasie, PA (US)

( * ) Notice: Subject to any disclaimer, the term of this patent is extended or adjusted under 35 U.S.C. 154(b) by 0 days.

(21) Appl. No.: 09/733,681

(22) Filed: Dec. 1, 2000

(65) Prior Publication Data

US 2002/0107565 A1 Aug. 8, 2002

(51) Int. Cl.$^7$ .................................................. A61F 2/06
(52) U.S. Cl. ..................... 623/1.24; 623/1.13; 623/1.26; 623/2.14; 623/2.16; 623/2.18
(58) Field of Search ................................. 623/1.13, 1.14, 623/1.15, 1.24, 1.26, 2.14, 2.15, 2.16, 2.17, 2.18, 2.19, 2.38, 23.68

(56) References Cited

U.S. PATENT DOCUMENTS

| | | | | |
|---|---|---|---|---|
| 3,197,788 A | * | 8/1965 | Segger | 623/2.19 |
| 3,657,744 A | * | 4/1972 | Ersek | 128/898 |
| 3,744,062 A | * | 7/1973 | Parsonnet | 623/2.19 |
| 4,192,020 A | * | 3/1980 | Davis et al. | 623/2.13 |
| 4,265,694 A | * | 5/1981 | Boretos et al. | 623/2.19 |
| 4,417,360 A | * | 11/1983 | Moasser | 623/2.17 |
| 4,470,157 A | * | 9/1984 | Love | 623/2.15 |
| 4,787,899 A | * | 11/1988 | Lazarus | 623/1.14 |
| 5,411,552 A | * | 5/1995 | Andersen et al. | 137/343 |
| 5,522,881 A | * | 6/1996 | Lentz | 623/1.13 |
| 5,697,382 A | | 12/1997 | Love et al. | 128/898 |
| 5,855,601 A | * | 1/1999 | Bessler et al. | 623/2.38 |
| 5,957,949 A | * | 9/1999 | Leonhardt et al. | 606/108 |
| 6,254,564 B1 | * | 7/2001 | Wilk et al. | 623/1.24 |
| 2002/0032481 A1 | * | 3/2002 | Gabbay | 623/2.11 |

* cited by examiner

*Primary Examiner*—Paul B. Prebilic
(74) *Attorney, Agent, or Firm*—Synnestvedt & Lechner LLP

(57) ABSTRACT

A one-way valve suitable for implant in the human vascular system is disclosed. The valve is formed by a tube of braided filaments and has an upstream end supported in an open configuration by a radial support. The valve has a downstream portion formed by a plurality of flexible leaflets resiliently biased into a closed configuration sealing the valve. The leaflets separate under pressure to allow fluid flow downstream but close in response to back pressure to prevent retrograde flow. The leaflets are biased by internal elastic forces within the filaments or by means of a resilient flexible membrane. To prevent collapse of leaflets under relatively high back pressure, elongated support columns are arranged lengthwise along the tube. A second radial support is provided downstream to support the columns. Fasteners are positioned circumferentially around the tube to anchor the valve within the lumen of the vascular vessel.

16 Claims, 9 Drawing Sheets

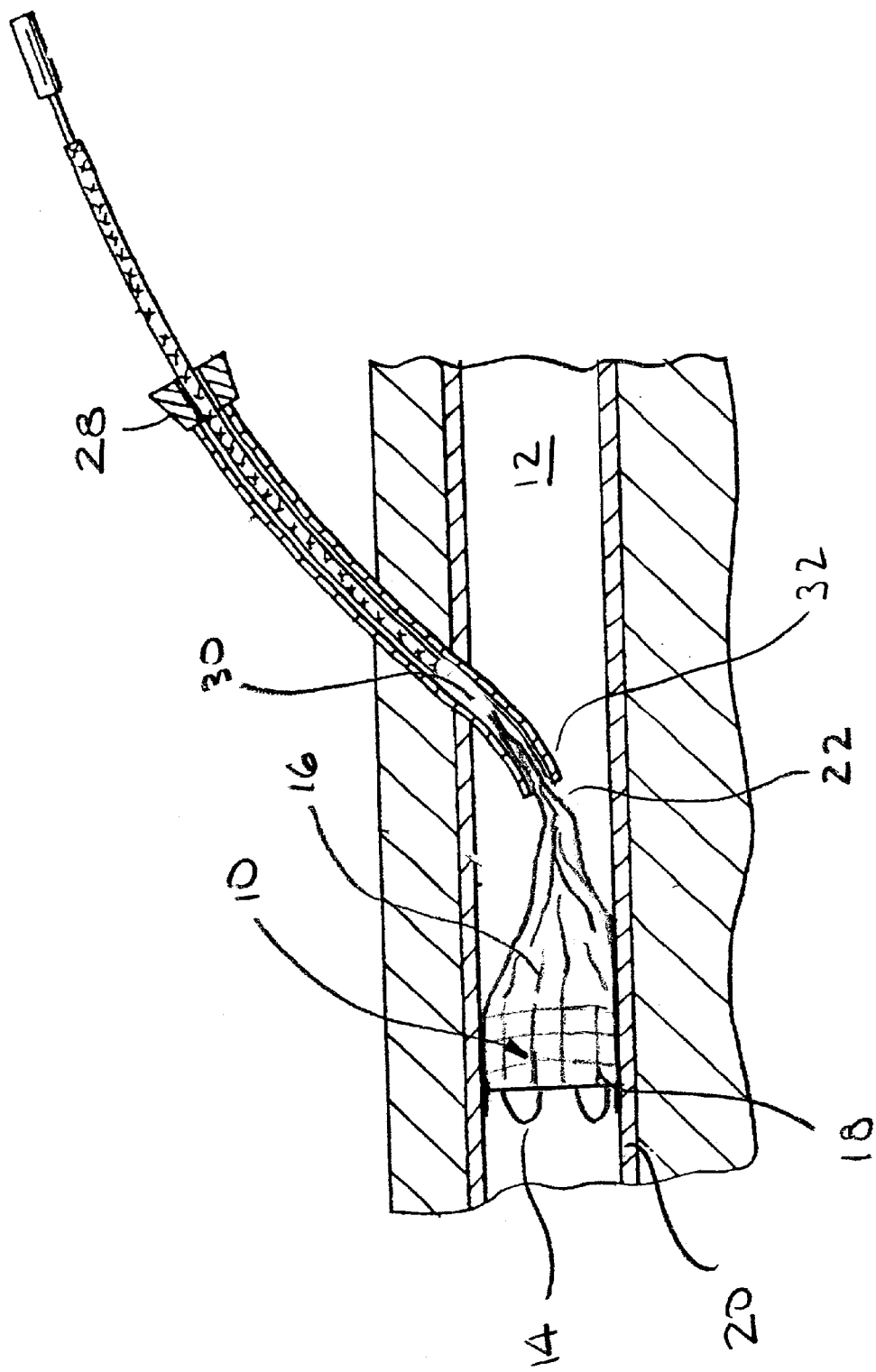

```
BRAID TUBE
    ↓
STRETCH TUBE
OVER MANDREL
    ↓
APPLY STENT TO
TUBE AND MANDREL
    ↓
COAT TUBE AND STENT WITH
FLEXIBLE, RESILIENT LAYER
    ↓
REMOVE TUBE AND
STENT FROM MANDREL
    ↓
TRIM TUBE TO SIZE
```

FIG. 5

ENDOVASCULAR VALVE

FIELD OF THE INVENTION

This invention relates to one-way valves and especially to replacement valves for use within the human circulatory system.

BACKGROUND OF THE INVENTION

The veins of the human circulatory system have one-way valves comprising two leaflets (known as bicuspid valves), which promote the flow of blood from the extremities back to the heart by preventing the retrograde flow of blood to the extremities between heart beats. The presence of the venous valves also allows muscular action to assist in the pumping of blood from the venous side of the circulatory system back to the heart. The contraction of various muscles tends to constrict the veins, forcing blood to flow, and the venous valves permit only one-way flow back to the heart.

The veins are subject to various disorders related to defective structure and function of their valves, known as valve incompetence. Valve incompetence can cause varicose veins, as well as chronic venous insufficiency wherein the valve leaflets become thickened and contracted so that they become incapable of preventing the retrograde flow of blood. Both of these conditions cause considerable discomfort and can lead to further complications such as edema, erythema, dermatitis, skin ulceration and cellulitis.

Tricuspid valves (having three leaflets) are found in the heart and enable the heart to act as a pump by allowing only one-way flow of blood. The heart valves are also subject to various disorders such as mitral stenosis, mitral regurgitation, aortic stenosis, aortic regurgitation, mitral valve prolapse and tricuspid stenosis. These disorders are serious, potentially life threatening and may be treated by surgical replacement of the affected valve.

Artificial endovascular valves for the replacement of incompetent venous valves or diseased heart valves should be bio-compatible, long-lasting, and have the appropriate hemodynamic characteristics which approximate those of natural valves to properly control and promote the flow of blood throughout the circulatory system. Such endovascular valves may also find use in artificial hearts and artificial heart assist pumps used in conjunction with heart transplants.

SUMMARY AND OBJECTS OF THE INVENTION

The invention concerns a one-way valve positionable within a lumen of a vessel, such as a vein. The valve according to the invention comprises a flexible tube formed of intermeshed filaments, which are preferably intermeshed by braiding. The tube has an upstream end and a downstream end which are oppositely disposed from each other. A radial support is attached to the tube at the upstream end. The radial support biases the tube radially outwardly into an open configuration which allows fluid within the vessel to flow relatively unimpeded into the valve from the upstream end. A plurality of flexible leaflets comprises the downstream end. The leaflets have surfaces facing inwardly of the tube. The leaflets are interengagable with each other and movable from a closed position wherein the surfaces are in sealing contact to stop flow through the valve in an upstream direction and an open position wherein the leaflets are separated apart from one another to permit fluid flow through the valve in a downstream direction. The leaflets are normally biased toward one another by a biasing means, allowing them to be readily moved into the closed position. Alternately, the leaflet may be biased into the closed position.

In one embodiment, the biasing means comprises the intermeshed filaments forming the tube themselves being resilient and biased by internal elastic forces into a converging shape wherein the surfaces of the leaflets are biased toward one another or in sealing contact. In the preferred embodiment, the biasing is provided by a resilient, flexible membrane covering the tube. The membrane has a converging shape which forces the surfaces of the leaflets toward each other or, alternately, into sealing contact. Preferably, the valve has two leaflets, although three leaflet valves are also feasible.

For higher pressure operations, it may be necessary to support the valve with one or more elongated supports arranged lengthwise along the tube. Preferably, the elongated supports are intermeshed with the filaments comprising the tube and prevent it from collapsing when subjected to pressure from the downstream end. The elongated supports may be integrally formed with the upstream radial support or may be connected between an upstream and a downstream radial support. Preferably, the radial supports push outwardly against the wall of the vessel to fix the valve in place. However, for relatively higher pressure applications fasteners having vessel engaging portions projecting outwardly from the tube may be used to fix the position of the valve by attaching it to the vessel wall.

It is an object of the invention to provide a one-way valve which can be implanted in a vessel of the human vascular system.

It is another object of the invention to provide a one-way valve which is compatible with human tissue.

It is yet another object of the invention to provide a one-way valve which is simple, inexpensive and long lasting.

It is still another object of the invention to provide a one-way valve which has hemodynamic characteristics similar to natural valves.

These and other objects of the invention will become apparent from a consideration of the following drawings and detailed description of the preferred embodiments.

DETAILED DESCRIPTION OF THE PREFERRED EMBODIMENT

Figure 1:
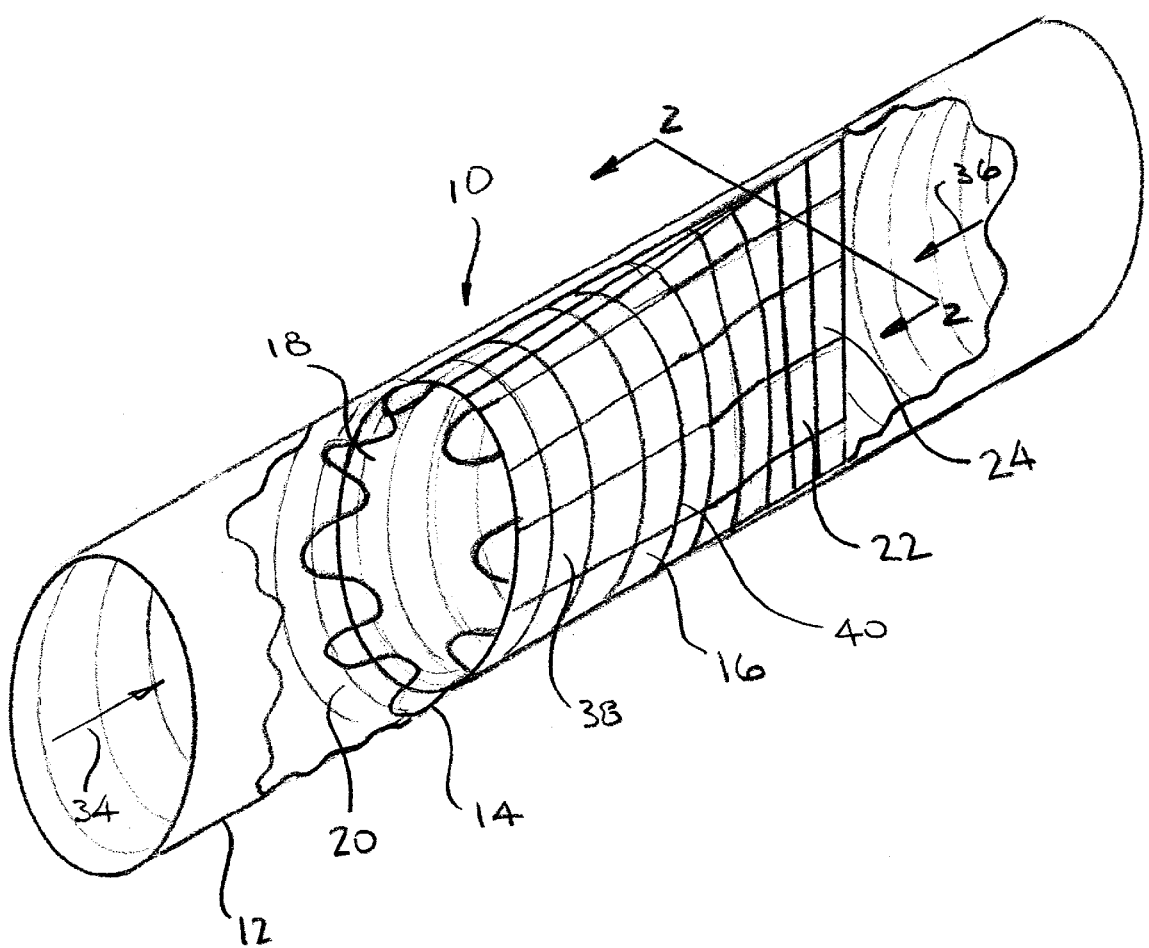
FIG. 1 is a perspective view of an endovascular valve according to the invention.

FIG. 1 illustrates an endovascular valve 10 according to the invention. Valve 10 is shown implanted within a vein 12 and comprises a radial support such as stent 14 attached to one end of an elongated flexible tube 16. Tube 16 is formed from interlaced filaments which are preferably intermeshed by braiding to provide inherent flexibility and conformity with a desired functional shape described below. The tube may also be formed by knitted or woven filaments. The term "filament" as used herein is a generic term for a continuous strand of fibers, yarns or material in a form suitable for braiding, knitting, weaving or otherwise intertwining to form a fabric. The term "filament" includes a number of fibers twisted together, a number of filaments laid together without twist, a number of filaments laid together with more or less twist, a monofilament and one or more strips made by a lengthwise division of a sheet of material.

Stent 14 is located at the upstream end 18 of the tube 16 and is preferably made of nitinol wire due to its properties of resilience, flexibility, strength and biocompatibility. However, other metals, such as stainless steel, elgiloy and spring steel, may also be used. Stent 14 supports tube 16 to maintain its upstream end 18 in a substantially circular, open shape. The stent also seals the valve 10 to vein 12 and helps hold the valve in position within the vein by pressing radially outwardly against the vessel wall 20. This prevents fluid from flowing around the valve and prevents the valve from moving in response to both static and dynamic pressure exerted by the blood flowing within vein 12. Stent 14 is preferably interbraided with the filaments comprising the tube 16 but may also be attached to it by sutures, adhesives or coatings described below.

Tube 16 is formed of polymer filaments, preferably polyester yarn, due to its tensile strength, toughness, flexibility, biocompatibility and long history of successful service in surgical implants. Other polymers, such as PTFE, polyurethane, FEP and silicone, may also be used, either alone or in combination, to form the tube.

In the preferred embodiment, the tube 16 is manufactured as a continuous tube of polyester yarns between 20 and 40 denier on a 144 carrier braiding machine. Choice of the yarn material, denier and braid density control the various properties of the valve such as flexibility, porosity, tensile strength, tear strength and burst pressure, all of which contribute to the hemodynamic characteristics of the valve.

Figure 2:
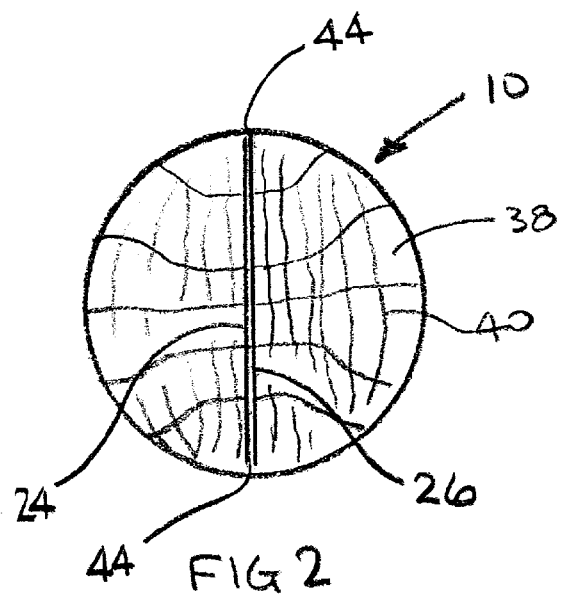
FIG. 2 is an end view of the valve shown in FIG. 1 taken along line 2—2.
Figure 4:
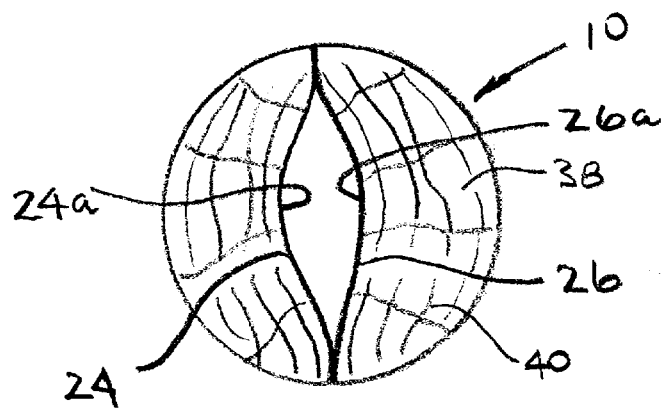
FIG. 4 is an end view of the valve shown in FIG. 2 but in the open position.

While the upstream end 18 of the tube is supported by the stent in an open, substantially circular shape, the downstream end 22 is biased into a converging shape by flattening of the tube wall, thereby forming two opposed, flexible leaflets 24 and 26 best shown in the end view of FIG. 2. For a "bicuspid" valve having two leaflets, the converging shape resembles a duckbill. As best shown in FIG. 4, leaflets 24 and 26 have surfaces 24a and 26a, respectively, which face inwardly of the tube and contact each other as shown in FIG. 2 to form a seal closing off the downstream end of tube 16. Biasing of the downstream portion into the converging shape may be accomplished by using resilient filaments to form the tube and biasing the filaments into the converging shape such that internal elastic forces within the filaments will naturally cause the tube to form the desired converging shape in the absence of external forces. Biasing of the filaments may be accomplished by stretching the braided tube over a mandrel having the desired converging shape and then heat setting the filaments at a predetermined temperature for a specified duration long enough to effect the biasing. For example, braided polyester yarn between 20 and 40 denier requires exposure to a temperature of 180° C. for about 5 minutes to effect the biasing of the yarns. For relatively small valves, the mandrel is 3–10 mm in diameter; for larger valves, 10–30 mm diameter. The tube, when pulled over the mandrel, adheres closely to the surface of the mandrel conforming substantially identically to its shape.

After the tube 16 has been heat set on the mandrel, it is cut to length, preferably by a laser, and the stent is attached to the upstream end 18, as described below.

Figure 3:
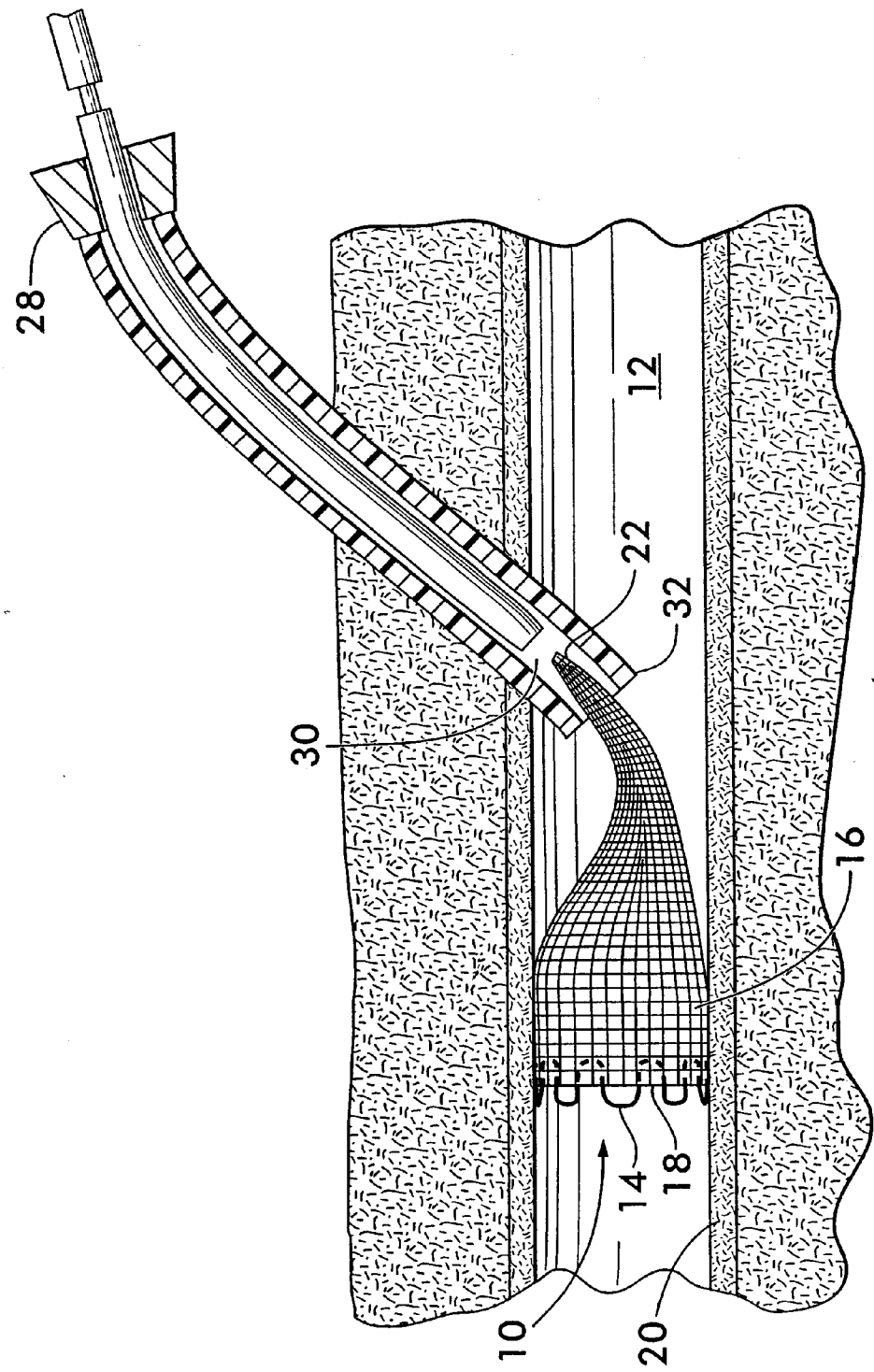
FIG. 3 is a longitudinal sectional view of a valve being implanted within a vessel.

Preferably, valve 10 is implanted in the vein 12 through the use of a catheter 28 as illustrated in FIG. 3. Valve 10 is collapsible to fit within the lumen 30 of the catheter. The catheter is then snaked into the vein 12 with its tip 32 positioned at the desired location to implant the valve. The valve is forced out of the catheter upstream end 18 first. Preferably, the stent 14 is resiliently biased and expands radially upon release from the catheter to open the upstream end 18 of the tube 16 into the substantially circular shape, the stent pushing radially against the vessel wall 20 and lodging the valve in the desired position. Alternatively, the stent may be radially expanded by a balloon prepositioned within the valve, the balloon being inflated when the valve is released from the catheter to inelastically expand the stent within the vein. Because the expansion is inelastic, the stent maintains its expanded diameter independently so that the balloon may be deflated and retracted into the catheter for removal with the catheter from the vein.

Once positioned within the vein, the valve operates to prevent retrograde flow of blood by virtue of the functional shape of the tube 16. As seen in FIG. 1, blood flowing under pressure toward the heart as indicated by the arrow 34 enters the open, upstream end 18 and travels through the tube 16 between leaflets 24 and 26 (see also FIG. 2). The blood pressure within the valve causes the leaflets to part as best illustrated in FIG. 4, and the blood is permitted to flow relatively uninhibited toward the heart. The leaflets 24 and 26 will pulse open with each heartbeat or with the muscular constriction of the vein. The leaflets reclose to assume their preferred biased shape between beats or constrictions when the pressure drops off. The flexibility and biasing of the leaflets, their shape and surface roughness are among the factors which determine the hemodynamic characteristics of the valve. The leaflets must be flexible enough to part readily and open under the pressure pulse to permit relatively unrestricted flow and also be biased sufficiently to close reliably between pulses for the endovascular valve to operate effectively as a one-way valve.

Due to its functional converging shape, the valve's leaflets 24 and 26 will be forced together to close and seal the valve when the valve encounters a pressure pulse tending to force the blood in a retrograde direction away from the heart as indicated by arrow 36. Thus, retrograde motion of the blood is prevented by the valve analogous to natural venous bicuspid valves. The leaflets need not be biased into the closed shape with the surfaces in sealing contact. For efficient operation, it is enough that they be biased toward one another and readily allow the surfaces to come into contact as a result of the retrograde pressure pulse substantially in the manner of natural bicuspid valves.

Because the valve is comprised of intermeshed filaments, interstices formed between the filaments will cause the tube 16 to have a certain degree of porosity. The porosity is determined by the diameter and the number of filaments per inch of valve circumference. Ideally the valve should have no porosity and, thus, allow no retrograde blood flow. There are at least two advantageous methods of eliminating the porosity. In one method, endothelial cells, which form the internal lining of the vein, grow into the interstices and eliminate the tube's porosity. In the preferred embodiment of the valve (described below), a silicone coating on the tube seals the interstices.

Figure 5:
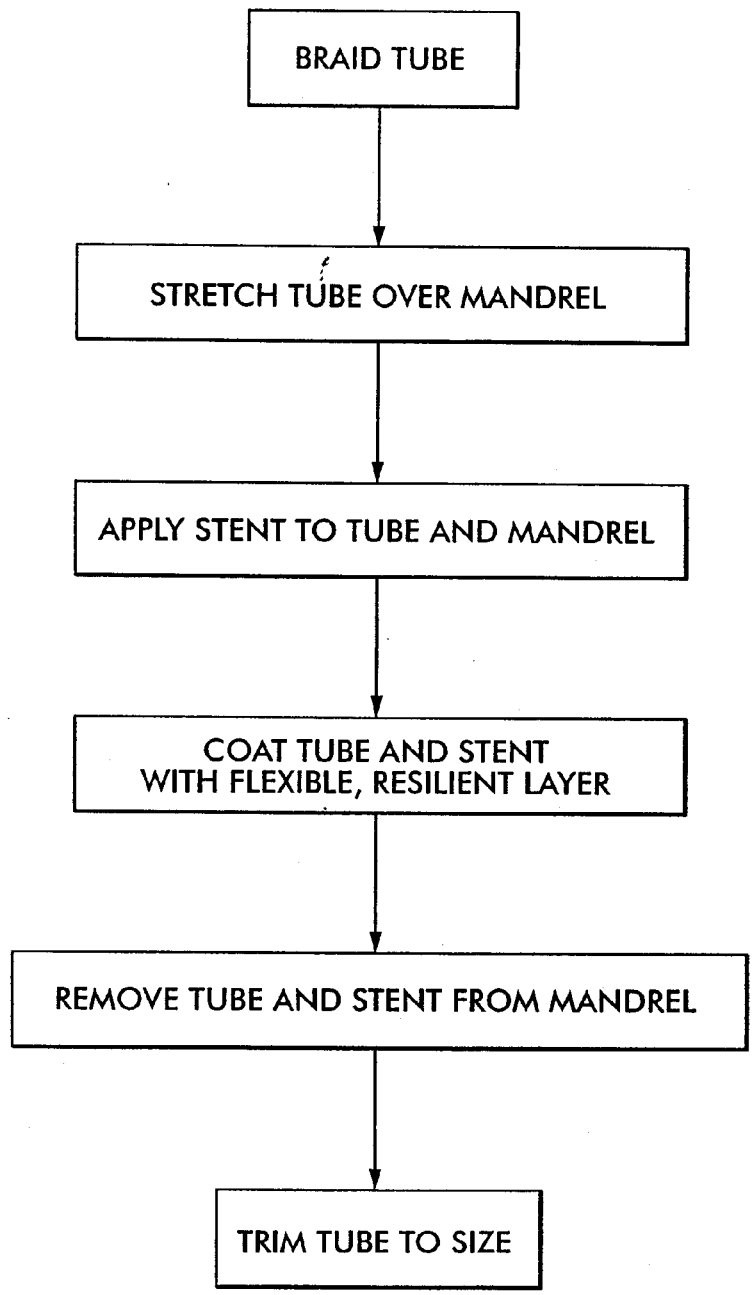
FIG. 5 is a flow chart depicting a process for manufacturing a valve according to the invention.
Figure 6:
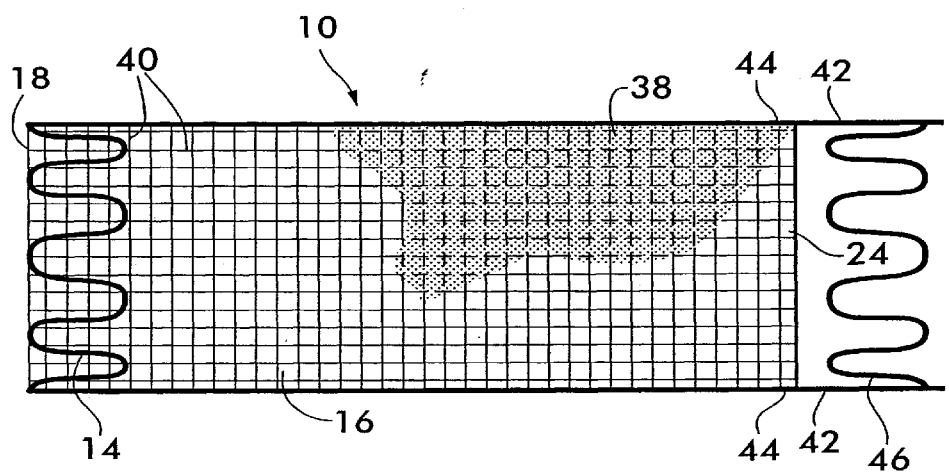
Figure 7:
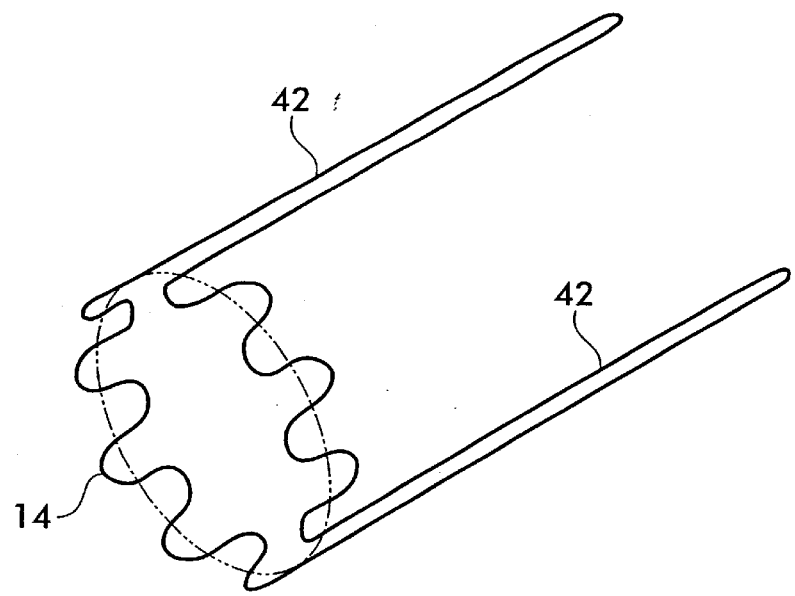
Figure 9:
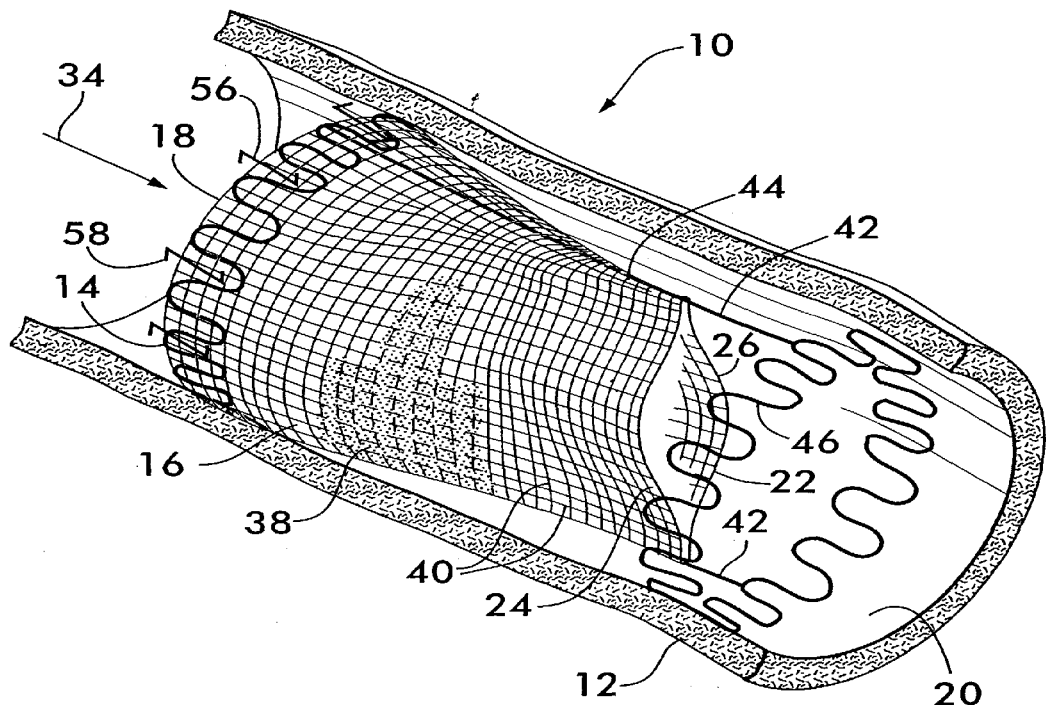
Figure 10:
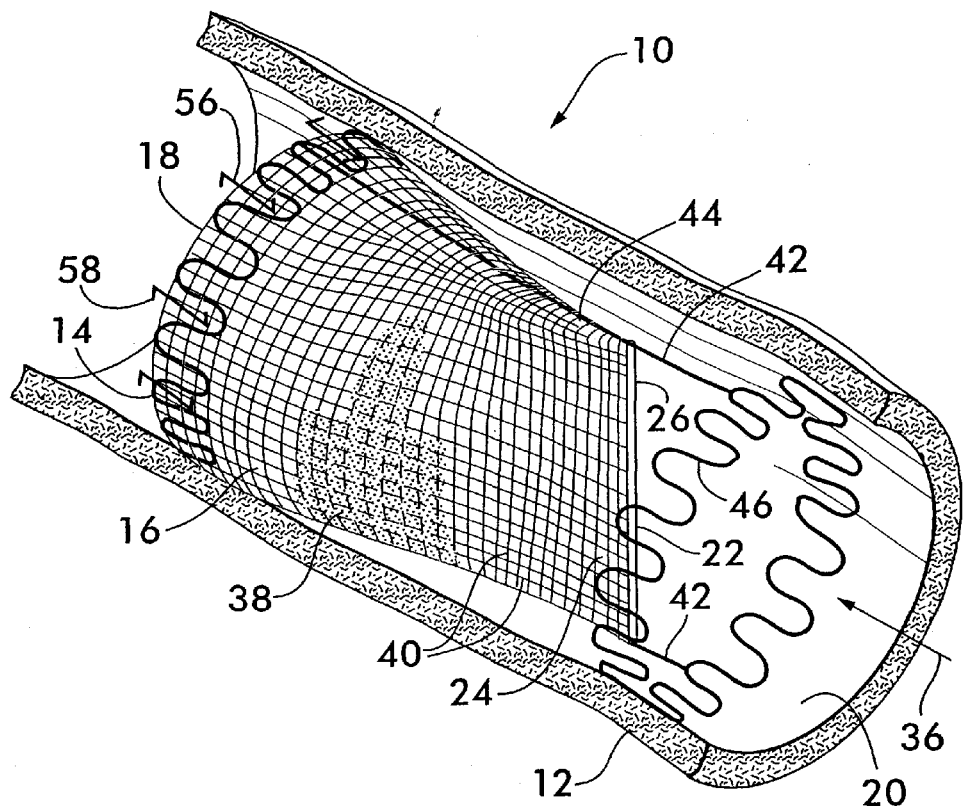
Figure 11:
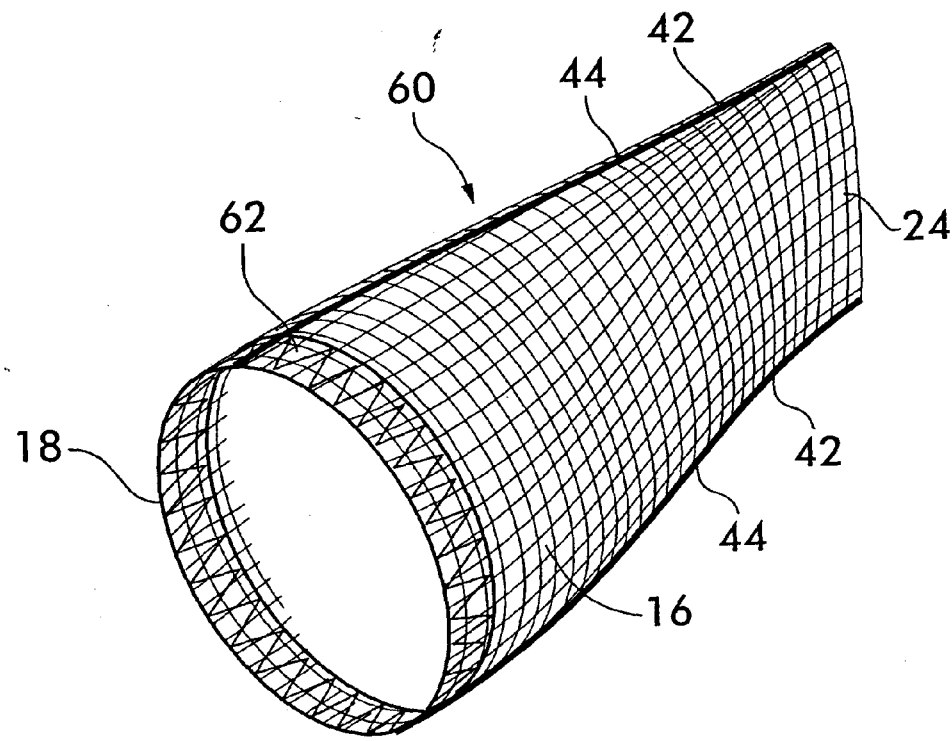
Figure 1:
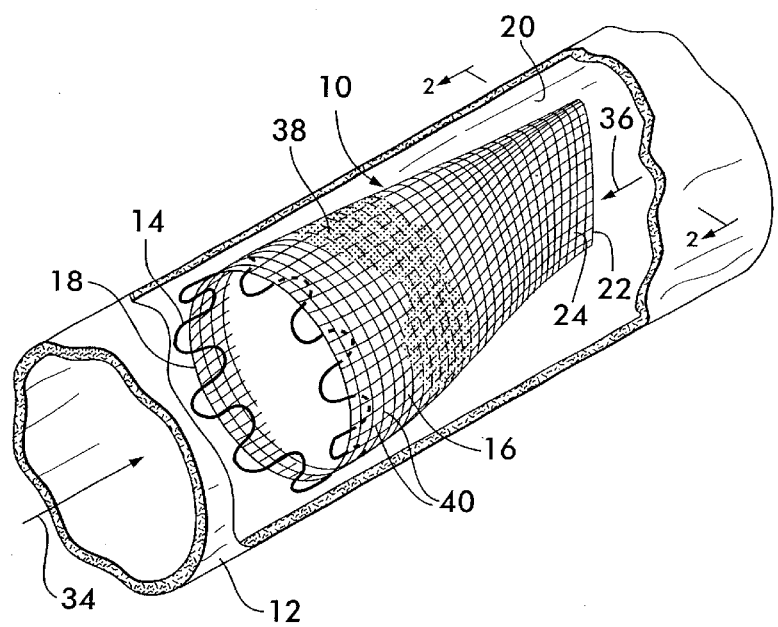
Figure 2:
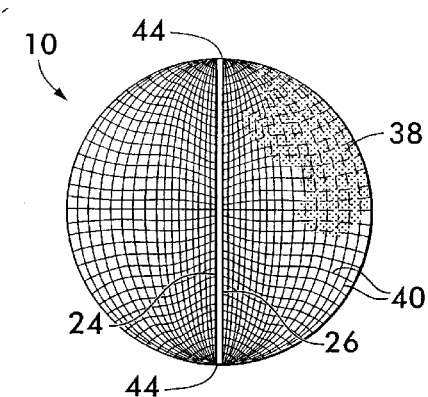
Figure 4:
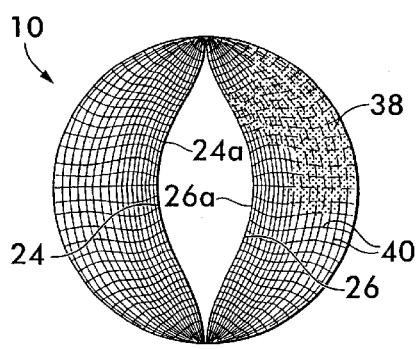
Figure 8:
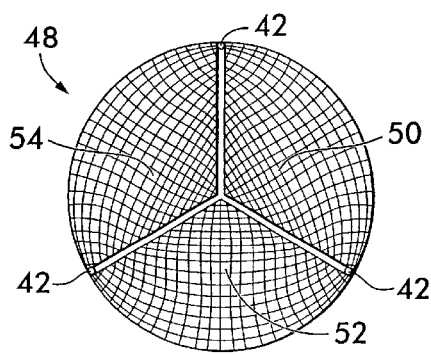
Figure 5:
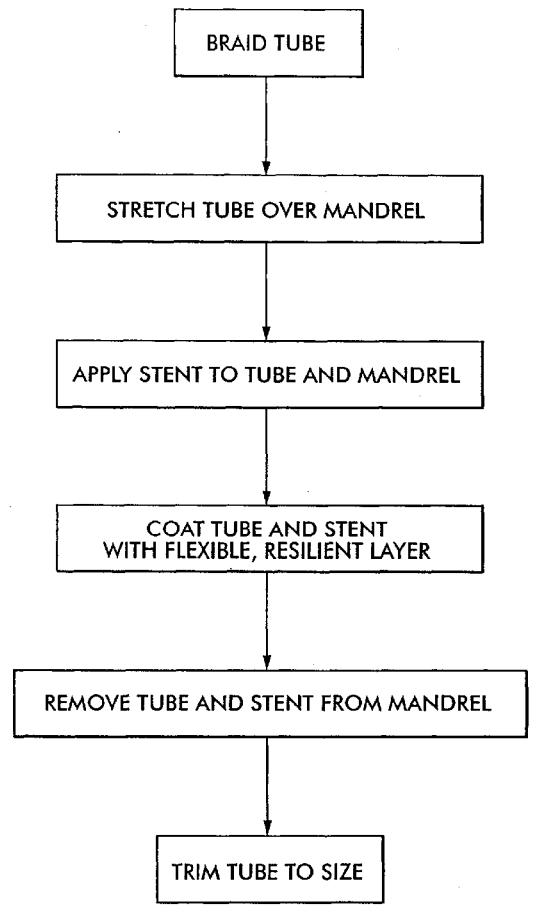
Figure 6:
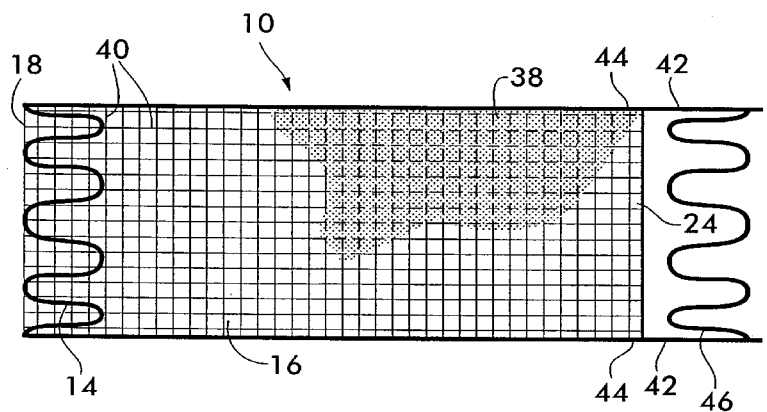
Figure 7:
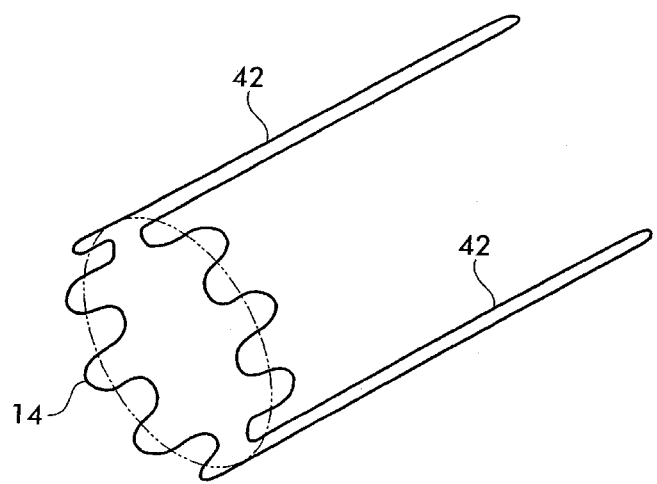
Figure 9:
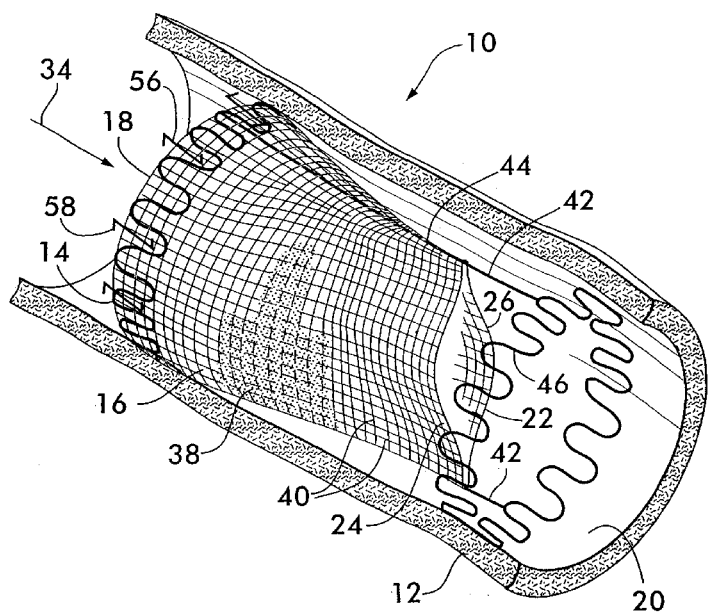
Figure 10:
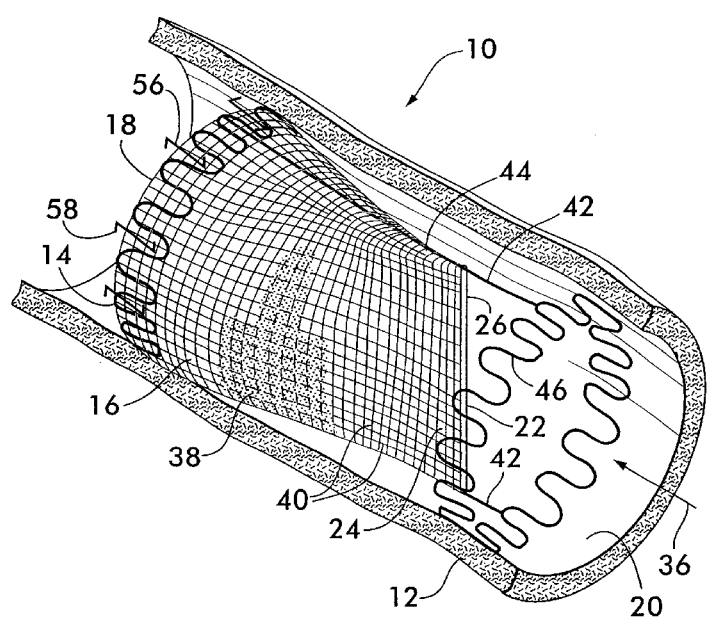

The preferred embodiment of the valve 10 is a bicuspid valve formed from a continuous tube of intermeshed (preferably braided) filaments which are stretched over a mandrel having the converging shape. As described above, the tube adheres tightly to the surface of the mandrel, assuming its shape. The stent 14 is also positioned on the mandrel in contact with the tube at what will be the upstream end of the valve, and the tube is then coated with a flexible, resilient layer, preferably a silicone compound. The coating process can be effected by dipping the mandrel, tube and stent into a reservoir of silicone or by spraying the compound onto the aforementioned components. Upon curing of the silicone, the valve is then removed from the mandrel and cut to size, again preferably by a laser. FIG. 5 presents a flow chart of the preferred manufacturing process.

In the preferred embodiment described above, the flexible, resilient layer performs several functions. First, it eliminates the porosity of the tube by filling in the interstices between the filaments. The tube 16 is thus comprised of a flexible, resilient silicone membrane 38 reinforced by a scrim cloth 40 of intermeshed filaments. The filaments strengthen the membrane and provide potentially variable parameters, such as filament material, denier and mesh density, to help control the mechanical properties of the tube 16. The mechanical properties, such as stiffness, tensile strength, tear strength and bursting strength, all affect the hemodynamic characteristics of the valve 10 and can be tailored so that the endovascular valve approximates the behavior of a natural venous or heart valve.

Second, the member 38 serves to bias the tube 16 into the converging shape required for sealing contact of the leaflets. This shape is taken from the mandrel, and upon curing, the flexible, resilient membrane always wants to return to this shape when not subjected to pressures or forces tending to distort it. The resiliency of the membrane allows the valve to distort, thus, permitting the leaflets 24 and 26 to separate (see FIG. 4) when under a pressure pulse from blood flow toward the heart, but resiliently returning the leaflets to the closed position (FIG. 2) or nearly so after the pulse is completed.

Third, the membrane 38 prevents the tube 16 from unraveling and serves to bind the stent to the tube like an adhesive.

Figure 6:
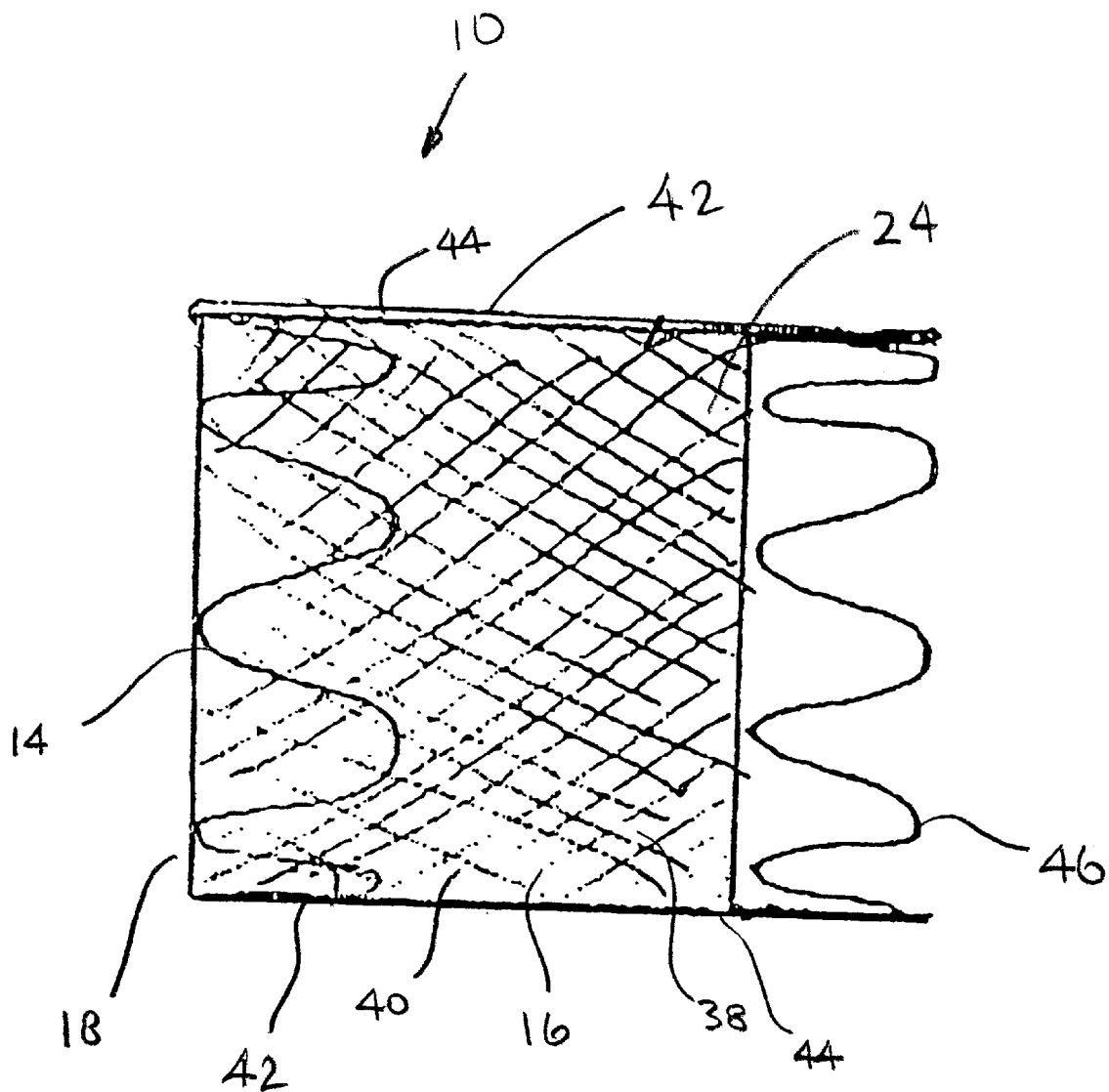
FIG. 6 is a side view of an alternate embodiment of an endovascular valve according to the invention.

The embodiments of the endovascular valve thus far described are suitable for relatively lower pressure applications as may be encountered on the venous side of the human circulatory system. However, under higher pressures, such as may be encountered on the arterial side of the circulatory system, or in an artificial heart, the back pressure against the closed valve may be sufficient to cause the leaflets to collapse inwardly upon themselves, turning the valve "inside out". In this condition, the valve no longer operates to prevent retrograde blood flow. To prevent this failure mode, elongated supports, preferably in the form of support columns 42, seen in FIG. 6, are provided which extend from stent 14 along the length of tube 16. The columns 42 are preferably positioned along the folds 44 between the leaflets 24 and 26 (see also FIG. 2) to increase the stiffness of the valve to prevent collapse under back pressure without adversely affecting the flexibility of the leaflets to open and close as necessary for proper valve functioning.

Figure 7:
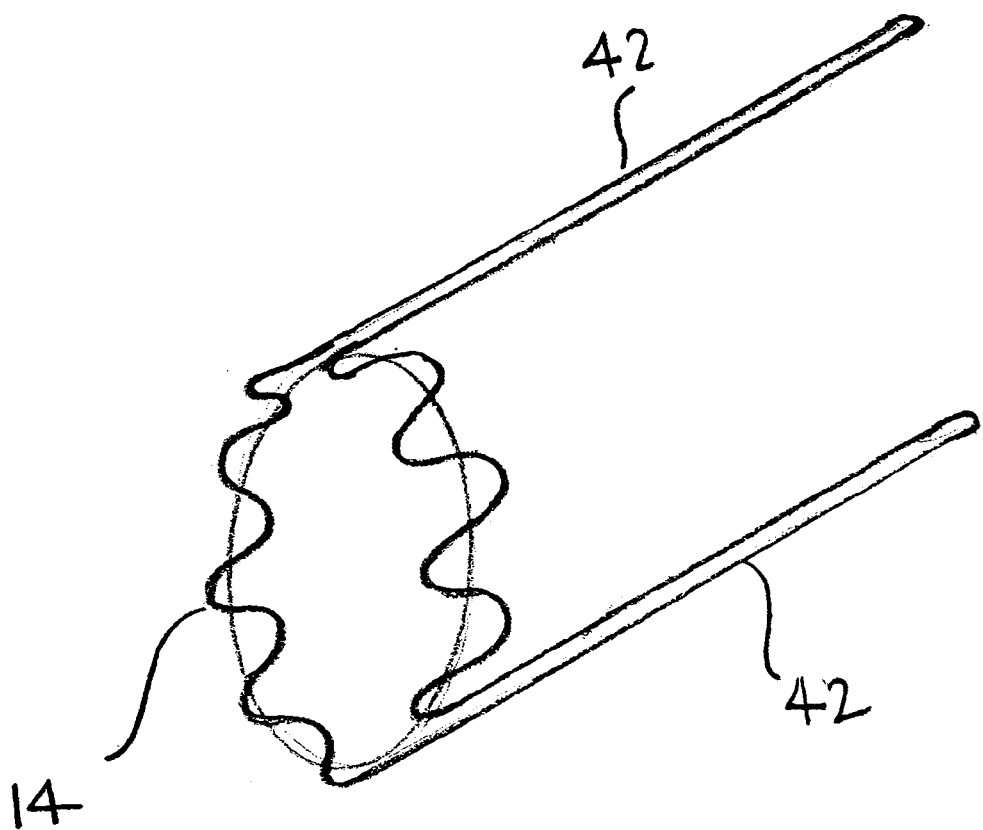
FIG. 7 is a perspective view of a stent with integral supporting columns for use with an endovascular valve according to the invention.

Support columns 42 are preferably formed of nitinol due to its biocompatibility, flexibility and resilience and may be bonded, welded or integrally formed as extensions of stent 14 as seen in FIG. 7. Further support of the ends of the support columns distal to stent 14 may be necessary and is preferably provided by a second stent 46 or other radial support attached to the columns. Stent 46 is preferably made of nitinol similarly to stent 14 but could also be formed of eligloy, stainless steel or other flexible, resilient, elastic biocompatible material. Stent 46 is collapsible similarly to stent 14 to allow the valve embodiment shown in FIG. 6 to be delivered into a vessel via a catheter as previously described.

Figure 8:
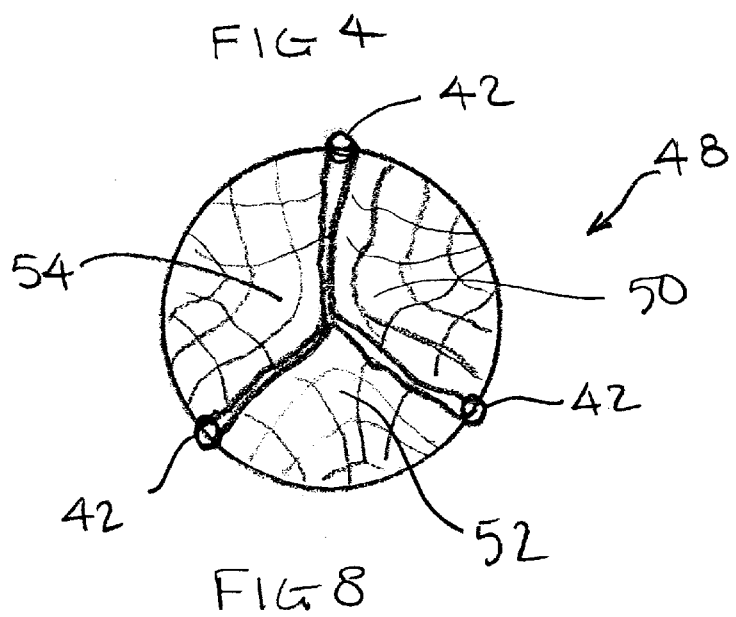
FIG. 8 is an end view of a tricuspid endovascular valve according to the invention.

In forming the valve 10, the support columns, when used, are preferably interbraided with the filaments forming the tube. In the example of the 144 carrier braiding machine cited above, two axial ports are provided in the braider to interbraid two axially extending support columns in the bicuspid valve. Additional support columns may also be incorporated, as shown in FIG. 8, for the tricuspid valve 48 which has three leaflets 50, 52 and 54 and three support columns 42. The tricuspid valve is favored for higher pressure applications such as heart valve replacements or as valves in artificial hearts. The multiple leaves do not deflect as much during opening and closing and thus do not wear out as rapidly, providing a longer lasting valve. Due to their smaller size, the leaflets of the tricuspid valve can open and close more rapidly in closer response to the frequency of the pressure pulses, thus, providing increased efficiency in preventing retrograde flow when compared with the slower operating bicuspid valve.

Figure 9:
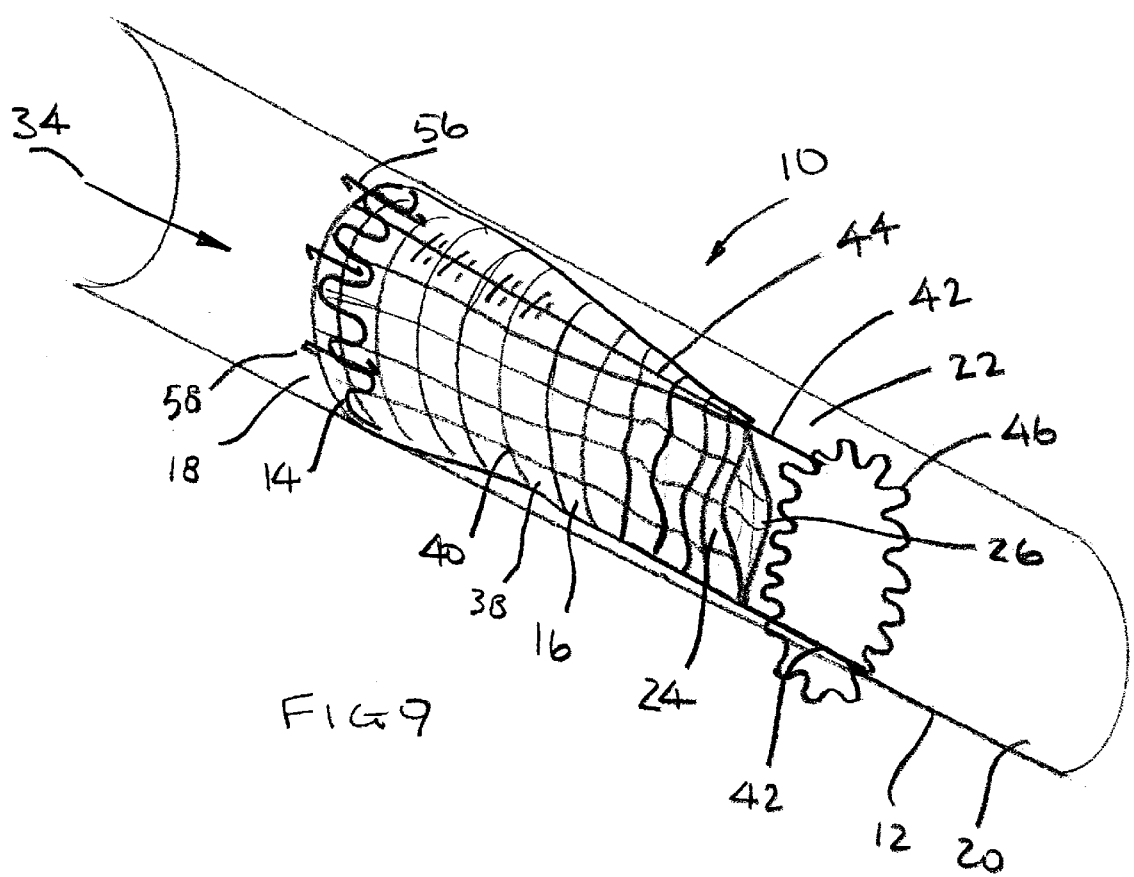
FIG. 9 shows a perspective view of the valve embodiment of FIG. 6 in the open position.
Figure 10:
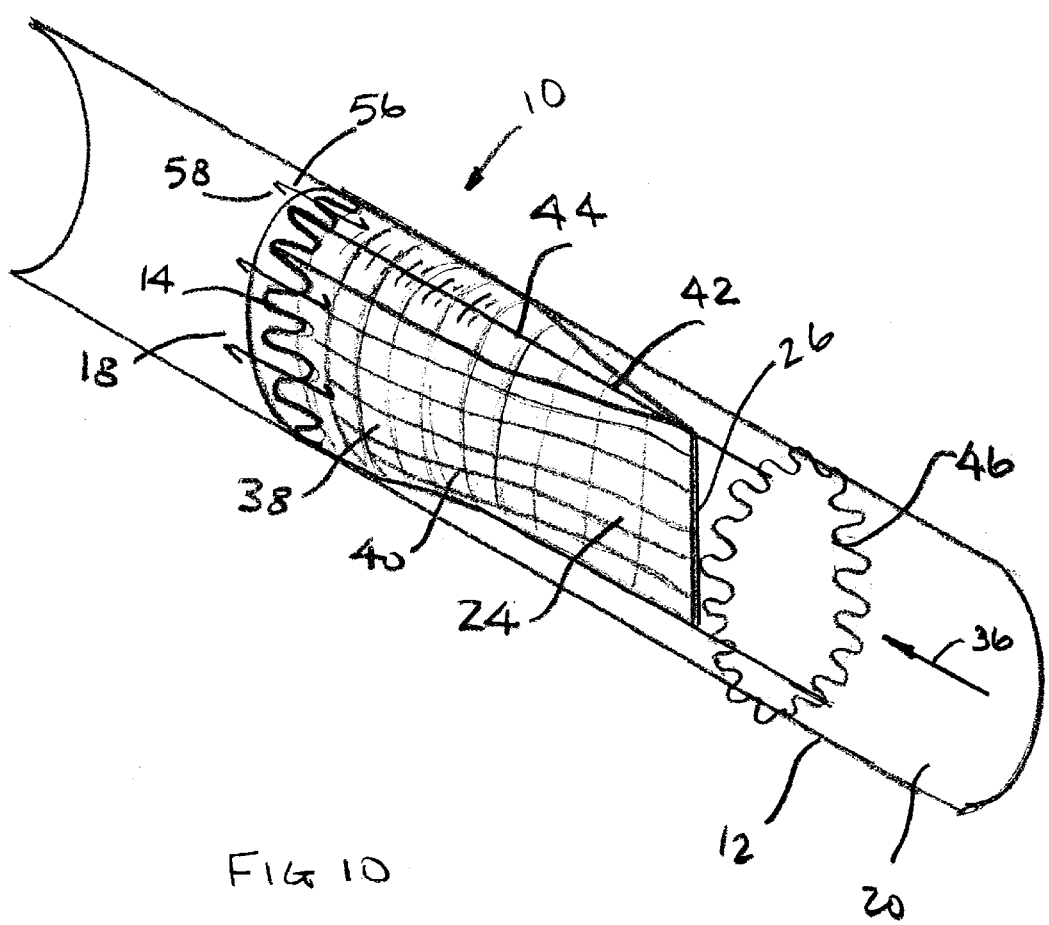
FIG. 10 shows a perspective view of the valve shown in FIG. 9 in the closed position.

FIGS. 9 and 10 illustrate a biscupid-type valve 10 with support columns 42 according to the invention in operation within vein 12. In FIG. 9, the valve is shown in the open position with leaflets 24 and 26 separated as a pressure pulse forces blood through the valve in the direction 34 towards the heart. The closed valve is shown in FIG. 10 with the leaflets being biased back into their closed position, any back pressure tending to cause retrograde flow in the direction of arrow 36 forcing the leaflets together tighter, thereby increasing the sealing effect between the leaflets preventing the retrograde flow.

Stents 14 and 46 support the valve and hold it in position within the vein by pressing radially outwardly against the vessel wall 20. However, this may not be enough to hold the valve in place against the pressure. To prevent motion of the valve within the vein, a plurality of fasteners, such as hooks 56, are attached to the valve, preferably circumferentially around the upstream end 18 of the tube. Hooks 56 may be sutured to the tube 16, welded to the stent 14, interbraided with the scrim cloth 40 or sealed in place by the resilient membrane 38. The hooks have vessel-engaging portions 58 which project outwardly from the tube and dig into the vessel wall 20 and resist motion of the valve relative to the vein 12 due to the pressure pulses pumping the blood. The hooks may have vessel-engaging portions 58 at both ends facing in opposite directions to prevent movement of the valve in either direction, since pressure pulses will come from either side of the valve.

Figure 11:
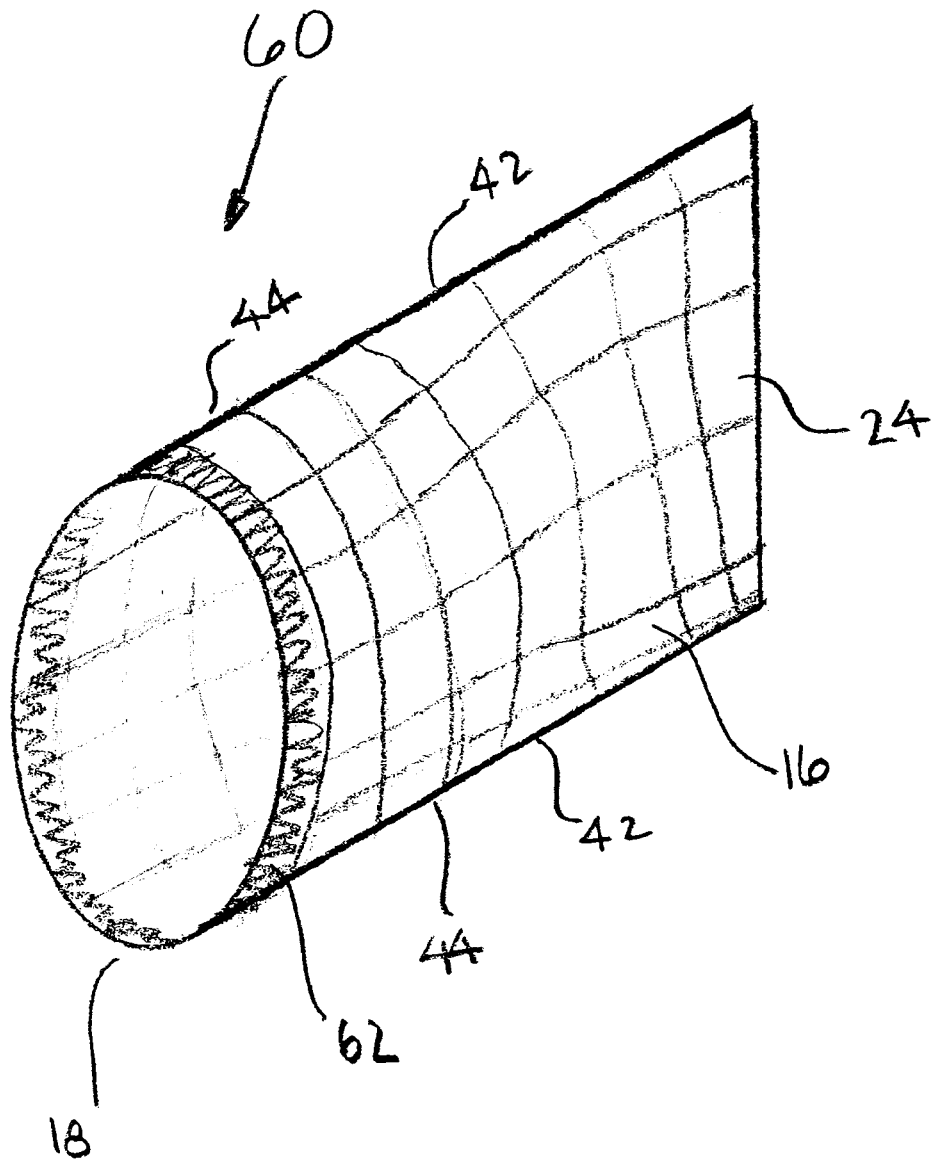
FIG. 11 shows another embodiment of the endovascular valve according to the invention.
Figure 1:
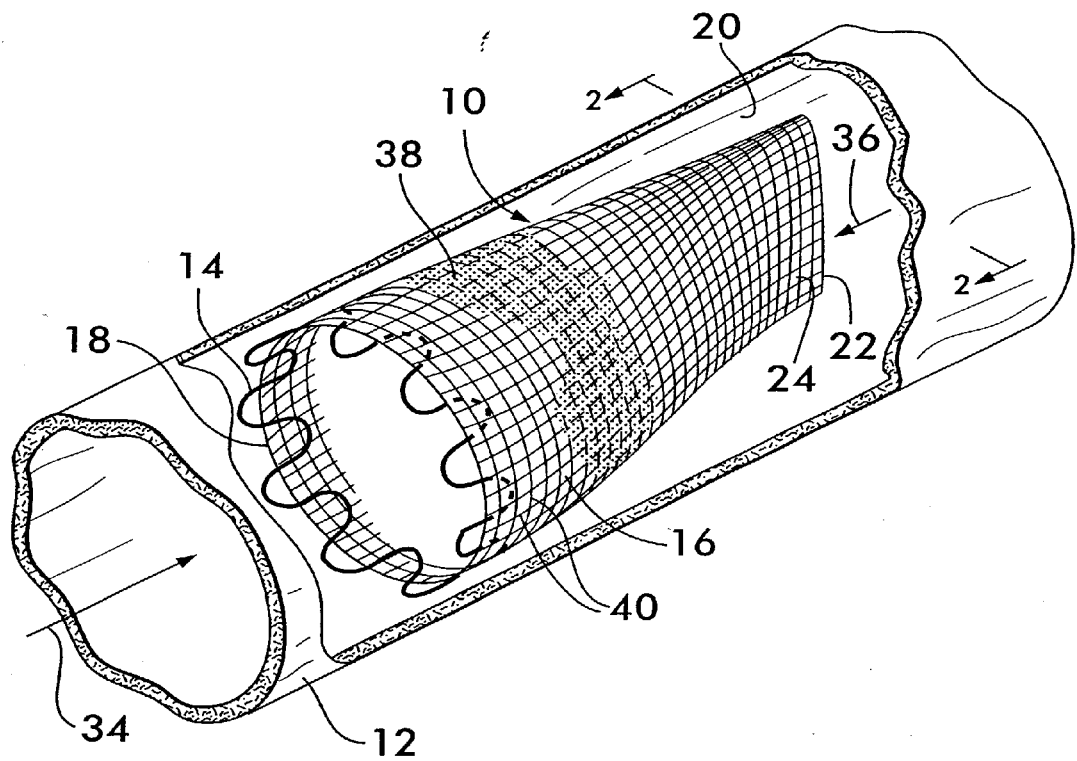
Figure 2:
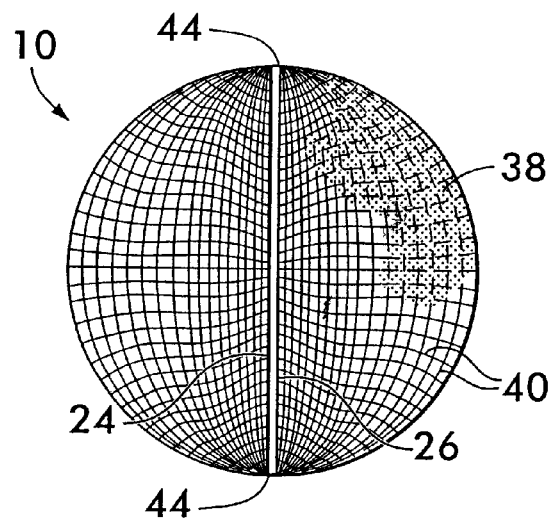
Figure 4:
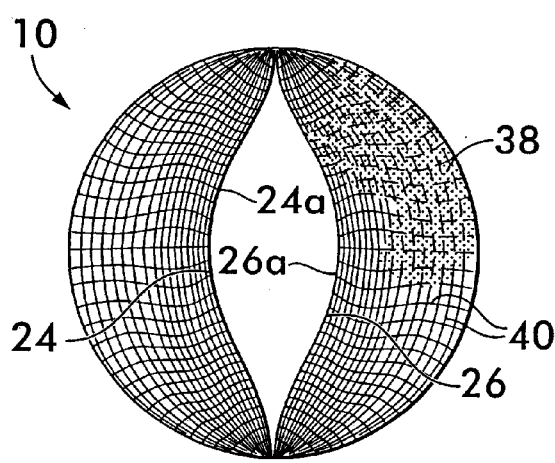
Figure 8:
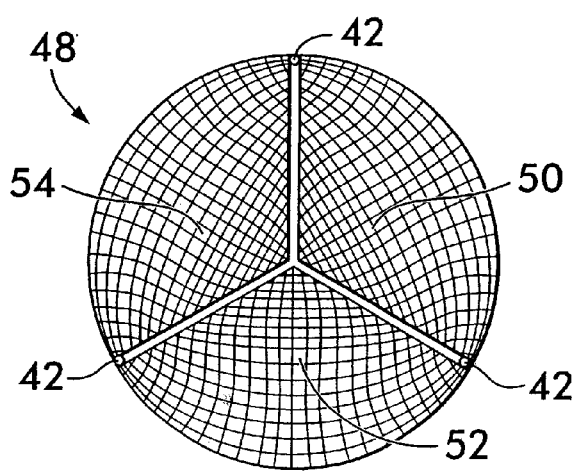

Another embodiment of the endovascular valve according to the invention is shown at 60 in FIG. 11. Valve 60 is a bicuspid valve having two leaflets 24 and 26 (26 not visible)

and two support columns 42 arranged along folds 44. The tube 16 may be comprised of the relatively simple intermeshed filaments or formed of the scrim cloth and flexible, resilient membrane as described above. A cuff 62 is positioned at the upstream end 18 of the membrane portion. The cuff provides a thickened, reinforced region of increased strength for accepting sutures for surgically attaching the valve to a vessel. The cuff 62 may be formed in any number of ways, for example, by rolling the scrim or intermeshed material at the upstream end back upon itself or by knitting a cuff portion and then changing the knitting pattern to produce the cylindrical tube integrally formed with the cuff.

The endovascular valve according to the invention provides an artificial valve suitable for implantation in the human body or for use with an artificial heart or various heart transplant assist devices. The endovascular valve characteristics can be tailored to approximate the hemodynamic properties of natural valves and should provide the advantages of simplicity of design and cost effectiveness over artificial valves currently in use.

What is claimed is:

1. A one-way valve positionable within a lumen of a vessel by means of a catheter, said one-way valve comprising:
    a flexible tube formed of filaments intermeshed by braiding and having an upstream end and a downstream end oppositely disposed;
    an upstream radial support attached to said tube at said upstream end, said upstream radial support being collapsible to fit within the catheter and resiliently biased to expand radially outwardly upon release from the catheter to push radially against the vessel, said upstream radial support biasing said tube radially outwardly into an open configuration upon being expanded;
    said downstream end of said tube being formed into a plurality of flexible leaflets, said leaflets having surfaces facing inwardly of said tube and interengagable with each other, said leaflets being movable from a closed position wherein said surfaces are in sealing contact, and an open position wherein said leaflets are separated apart from one another; and
    means for flexibly biasing said leaflets toward one another.

2. A valve according to claim 1, wherein said surfaces are biased into said sealing contact.

3. A valve according to claim 1, wherein said filaments comprise polyester yarns between 20 and 40 denier.

4. A valve according to claim 1, wherein said upstream radial support comprises a stent extending circumferentially around said tube.

5. A valve according to claim 4, wherein said stent is resiliently biased to support said upstream end in said open position.

6. A valve according to claim 1, wherein said biasing means comprises said intermeshed filaments being resilient and biased by internal elastic forces into a converging shape wherein said surfaces of said leaflets are positioned adjacent to each other.

7. A valve according to claim 6, having only two said leaflets.

8. A valve according to claim 1, wherein said biasing means comprises a resilient, flexible membrane covering said tube, said membrane having a converging shape forcing said surfaces of said leaflets into a position adjacent to one another.

9. A valve according to claim 8, wherein said membrane comprises a silicone layer.

10. A valve according to claim 1, further comprising a first elongated support attached lengthwise along said tube for preventing said tube from collapsing under pressure applied from said downstream end within said lumen.

11. A valve according to claim 10, wherein said first elongated support is intermeshed with said filaments.

12. A valve according to claim 11, wherein said first elongated support is attached to and extends downstream from said upstream radial support.

13. A valve according to claim 12, wherein said first elongated support is integrally formed with said upstream radial support.

14. A valve according to claim 10, further comprising a second elongated support attached lengthwise along an opposite side of said tube from said first elongated support, and a downstream radial support positioned downstream of said upstream radial support, said first and second elongated supports being attached to each of said upstream and downstream radial supports.

15. A valve according to claim 1, further comprising a cuff located at said upstream end of said tube, said cuff comprising a thickened reinforced region of said tube for facilitating attachment of said valve to said vessel.

16. A valve according to claim 1, further comprising a plurality of fasteners mounted circumferentially around said tube, said fasteners having vessel engaging portions projecting outwardly from said tube for fixedly positioning said one-way valve within said vessel.

* * * * *

UNITED STATES PATENT AND TRADEMARK OFFICE
CERTIFICATE OF CORRECTION

PATENT NO.   : 6,494,909 B2
DATED        : December 17, 2002
INVENTOR(S)  : Greenhalgh It is certified that error appears in the above-identified patent and that said Letters Patent is hereby corrected as shown below:

Drawings,
Substitute figs 1-11 with the attached figs 1-11

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,494,909 B2
DATED         : December 17, 2002
INVENTOR(S)   : Greenhalgh It is certified that error appears in the above-identified patent and that said Letters Patent is hereby corrected as shown below:

Drawings,
Substitute figs 1-11 with the attached figs 1-11

Signed and Sealed this

Fourteenth Day of October, 2003

JAMES E. ROGAN
*Director of the United States Patent and Trademark Office*

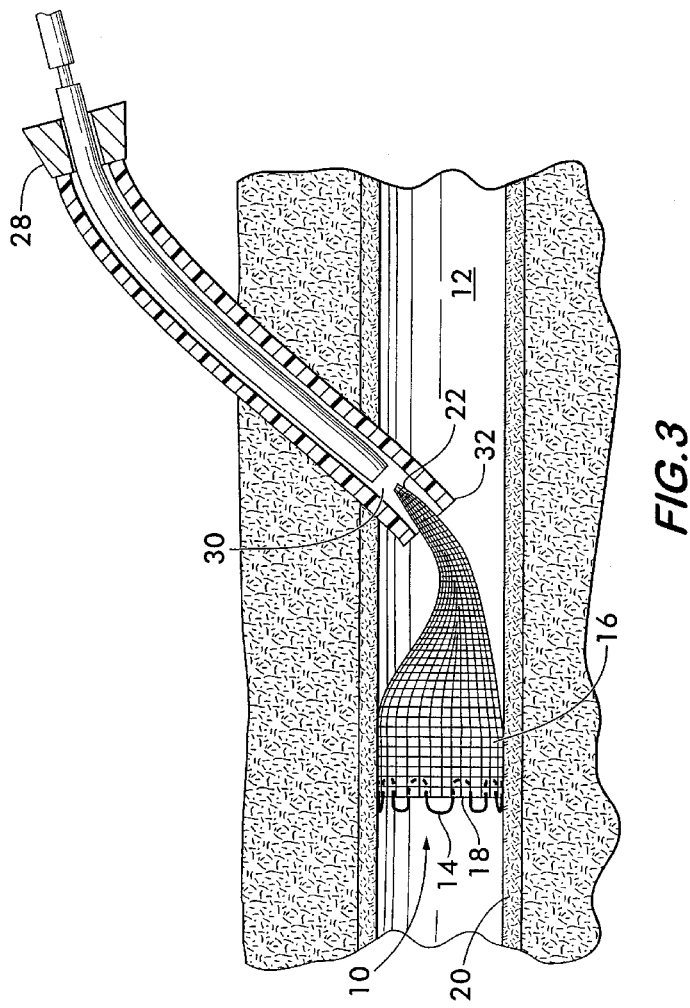

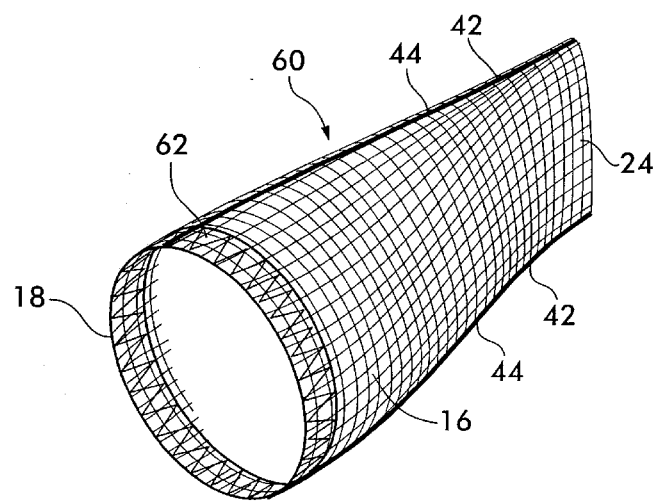
*FIG.II*